United States Patent [19]

McCormick

[11] Patent Number: 4,760,017
[45] Date of Patent: Jul. 26, 1988

[54] ARABINONUCLEIC ACID PROBES FOR DNA/RNA ASSAYS

[75] Inventor: Randy M. McCormick, Wilmington, Del.

[73] Assignee: E. I. Du Pont de Nemours and Company, Wilmington, Del.

[21] Appl. No.: 812,574

[22] Filed: Dec. 23, 1985

[51] Int. Cl.$^4$ .................. C12Q 1/68; C07H 15/12
[52] U.S. Cl. ........................... 435/6; 435/7; 536/27; 536/28; 536/29; 935/78
[58] Field of Search ............ 435/6, 7; 935/78; 536/27, 28, 29

[56] References Cited

U.S. PATENT DOCUMENTS 4,093,714  6/1978  Tolman et al. .................. 536/27

OTHER PUBLICATIONS

Barascut-I Chemical Abstracts 102:7037u, (1985).
Barascut-II Chemical Abstracts 103:215690f, (1985).
Barascut-III Chemical Abstracts 102:149725x, (1985).
Gioli, Chemica Scripta 19, pp. 13–17, (1982).
Kwiatkowski et al., Chemical Abstracts 97:56171b, (1982).
Ikehara et al., Nature New Biology, 240, pp. 16–17, (1972).
Smrt, Coll. Czech. Chem. Comm., 32, pp. 3169–3176, (1967).
Devash et al., J. Biol. Chem., 259(6), pp. 3482–3486, (1984).
Mian et al., J. Med. Chem., 17(3), pp. 259–263, (1974).
Okabayashi et al., Cancer Research, 37, 619–624, (1977).

Primary Examiner—Sidney Marantz
Assistant Examiner—Robert Benson
Attorney, Agent, or Firm—George A. Frank

[57] ABSTRACT

A novel nucleic acid, arabinonucleic acid, is provided as a probe in nucleic acid assays. The arabinose moiety of the probe can be detected with anti-arabinose antibody-label conjugates.

3 Claims, No Drawings

ARABINONUCLEIC ACID PROBES FOR DNA/RNA ASSAYS

TECHNICAL FIELD

This invention is related to arabinonucleic acid and the use of this novel polynucleotide probe in DNA or RNA hybridization assays and especially to probes containing a binding site in every constituent nucleotide. This permits the attachment of a detection moiety to each nucleotide of the probe and thus leads to improved detection sensitivity.

BACKGROUND ART

Hybridization probes used in DNA and RNA assays are labeled in some fashion to facilitate detection of the duplex after the probe has hybridized with a complementary strand of "target" DNA or RNA in the sample under analysis. Most commonly, the probe can be labeled by enzymatically incorporating radio-labeled nucleotides on the 3' or 5' terminus of the probe. [A. M. Maxam et al., Meth. Enzymol. Volume 65, 499–560 (1980)]. Alternatively, higher levels of radiolabeled nucleotides can be incorporated by nick translation [P. W. J. Rigby et al., J. Mol. Biol. Volume 113, 237–251 (1977)]. This latter method possesses the inherent advantage of being able to incorporate one radioactive phosphorus per constituent nucleotide in the probe and thus assays using these probes are characterized by the most sensitive detection limits in hybridization assays. The obvious disadvantages of these probes are the hazards and inconveniences associated with the use of radioisotopes.

A second type of label involves enzymatically synthesizing a probe with a mixture of nucleotides containing a biotinylated pyrimidine base (uracil or adenosine) incorporated into one of the nucleotides [e.g., P. R. Langer et al., Proc. Natl. Acad. Sci. USA Volume 78, 6633–6637 (1981)]. Alternatively, biotinylated histone Hl proteins can be chemically crosslinked with bases in DNA to yield a labeled probe [M. Renz, EMBO J. Volume 2(6), 817–822 (1983)]. After hybridization of the probe to a complementary strand of target DNA, the hybrid is treated with a reporter molecule attached to avidin which binds tenaciously to the biotin moieties in the probe. The reporter can be either an opaque polymeric microsphere bound to avidin [O. C. Richards et al., Proc. Natl. Acad. Sci. USA Volume 76(2), 676–680 (1979)] or avidin-ferritin [A. Sodja et al., Nucl. Acids Res. Volume 5(2), 385–401 (1978)]. Each of these can be visualized via electron microscopy. Alternatively, the reporter may be an avidin-enzyme complex which when treated with the enzyme's substrate, will yield a visually detectable colored product [J. J. Leary et al., Proc. Natl. Acad. Sci. USA, Volume 80 4045–4049 (1983)]. Assays based on these probes obviate the use of radioactive materials; however, only about 2% of the nucleotides in a given probe molecule can be derivatized with a biotin moiety without reducing the specificity of the probe for its complementary strand of sample DNA. This reduction in specificity arises from modification of the ability of complementary bases to pair properly because of the presence of the biotin moiety. The reduced incorporation of label in these probes relative to radioactive probes results in a poorer detection sensitivity.

A third type of label is an enzyme directly attached to the probe such that after hybridization the enzyme in the hybrid is treated with substrate to yield a colored product. The enzyme can be bonded directly to bases in the probe [M. Renz et al., Nucl. Acids Res., Volume 12(8), 3435–3444 (1984)] or to bases in another strand of DNA complementary to a length of oligonucleotide chemically attached to the end of the probe [J. G. Woodhead et al., Biochem. Soc., Trans., Volume 12(2), 279–280 (1984)]. In the latter case, the probe is hybridized to complementary target DNA and this hybrid is treated with the oligonucleotide containing the enzyme labels. This strand of labeled oligonucleotide binds with the single-stranded tail of complementary DNA which had been chemically attached to the end of the probe. Visualization of the enzyme reporters is accomplished by conversion of the enzyme's substrate to colored product. The primary difficulties associated with this procedure arise from the low level of enzyme attachment and the loss of enzyme activity when subjected to the stringent conditions (e.g. elevated temperature, non-aqueous solvent) typically used in the hybridization protocol. A secondary difficulty associated with the latter of these labeling methods is the possibility that the synthetic strand of oligonucleotide containing the enzyme label might be complementary to a sequence of naturally-occurring nucleotides in the sample. Thus, in addition to pairing with the sequence of bases attached to the end of the hybridization probe, the enzyme-labeled oligonucleotide may bind nonspecifically to natural sequences of complementary bases and thus lead to background problems in samples used as negative controls or blanks.

A fourth type of label involves coupling a fluorophore either to bases in the constituent nucleotides of the probe [C. H. Yang et al., J. Biochem. Volume 13, 3615–3620 (1974)] or to the 3'-terminus [R. W. Richardson et al., Nucl. Acids Res. Volume 11(8), 6167–6184 (1983)] or to the 5'terminus [C. H. Yang et al., Arch. Biochem. Biophys., Volume 155, 70–81 (1973)] of the probe. As above, the sensitivity of these methods is limited by the small number of labels which can be incorporated into each copy of the probe.

A fifth type of label involves the use of an antibody directed against some antigenic determinant in the probe or in the target-probe duplex. In the former case, an antigenic determinant (e.g., biotin, bromine, N-acetoxy-N-2-acetylaminofluorene) is covalently coupled to bases in the nucleotide of the probe [e.g., L. Manuelidis et al., J. Cell Biol., Volume 95, 617–625 (1982)]. These antigenic determinants may interfere with specific hybridization and limit the utility of the probe. In the latter case, the double-stranded DNA-RNA hybrid itself is immunologically distinguishable from DNA-DNA and RNA-RNA duplexes [G. T. Rudkin et al., Nature, Volume 265, 472–473 (1977)]. The antigenic determinant in the probe-target duplex was detected with an antibodyfluorophore conjugate and fluorescence microscopy. The labeled probe can also be detected with antibodies to which an enzyme (L. Manuelidis et al., op. cit.) or colloidal gold [N. J. Hutchinson et al., J. Cell Biol., Volume 95, 609–618 (1982)] has been conjugated. Again, the ultimate sensitivity is limited by the number of labels available to detect a hybridization event.

The instant invention overcomes the limitation of the prior art by incorporating the maximal number of non-radioactive labels, one per nucleotide, into each probe with negligible effect on hybridization efficiency or specificity.

DISCLOSURE OF THE INVENTION

This invention involves a new nucleic acid, arabinonucleic acid.

The method of this invention for identifying nucleic acid sequences comprises the steps of:
(a) rendering the target nucleic acids single-stranded;
(b) immobilizing the single-stranded nucleic acids onto a support;
(c) allowing said single-stranded nucleic acids to hybridize with a single-stranded arabinonucleic acid probe;
(d) washing said support to remove arabinonucleic acid not incorporated into the hybrid formed on the support; and
(e) determining the presence of arabinonucleic acid in the hybrid formed on the support by contacting it with an antiarabinose antibody-label conjugate and detecting said label.

DESCRIPTION OF THE INVENTION

This invention involves the synthesis and use of a novel hybridization probe for DNA and RNA assays. This new probe, arabinonucleic acid (ANA), has an arabinose sugar replacing the conventional ribose or deoxyribose sugars found in RNA and DNA, respectively. This uncommon sugar provides binding sites for an antiarabinose antibody-label which can be used to detect selectively the arabinose sugar and thus any probe containing the sugar. The sugar arabinose is found only in this synthetic probe and not in any naturally-occurring DNA or RNA and, therefore, the detection antibody will bind only to the arabinose moieties in the probe.

The probe can be synthesized either chemically or enzymatically. Chemical synthesis involves the introduction of protective groups on the 2', 3' and 5' carbon atoms of the arabinose sugar in a nucleoside containing arabinose instead of ribose or deoxyribose. Such nucleosides are commercially available. The chemical nature and method of attaching the protective groups has been developed for ribonucleosides and deoxyribonucleosides [G. H. Hakimeliah et al., Can. J. Chem., Volume 60, 1106–1113 (1982)] and can be adapted for protection of the corresponding positions in arabinonucleosides [K. K. Ogilvie et al., Can. J. Chem., Volume 61, 1204–1212 (1983)]. Once the protection of the arabinonucleosides has been achieved, the chemical synthesis of the arabinonucleic acid probe can then proceed in the manner used for DNA and RNA probes, in that the correct nucleotides will be sequentially linked to form a chain of nucleotides which is complementary to a sequence of nucleotides in target DNA or RNA in the sample under analysis (M. H. Caruthers et al., in Genetic Engineering, J. Setlow, ed., Vol. 4, 1–17, 1982).

Nucleic acids to be analyzed have many sources. These include clinical specimens, various microorganisms such as bacteria, viruses, chlamydia, rickettsia, mycoplasma and protozoa, plants, among others. Extraction is one common method for collecting the nucleic acids from their sources for hybridization assays. The protocol for use of the ANA probes of this invention is much like that in conventional hybridization procedures. The target DNA or RNA is first rendered single-stranded and then immobilized onto a support. The immobilized single-stranded nucleic acids are then treated with the arabinonucleic acid probe complementary to a sequence of bases in the target. Hybridization of the arabinonucleic acid probe with the complementary sequence of bases is allowed to occur. After washing to remove excess unhybridized ANA probe, the probe-target hybrid is treated with an anti-arabinose antibody-label conjugate.

The antibody itself is raised against the C2 chiral site in arabinose or the C2 site in conjunction with other antigenic determinants in the arabinose or ANA structures [Okabayashi et al., Cancer Research Volume 37, 619–624 (1977)]. The antibody-conjugate can be prepared by conventional means. The label can be enzymatic, fluorescent, chemiluminescent or macromolecular, the preferred one being enzymatic.

This antibody-label conjugate specifically binds to the arabinose sugar but not to ribose or deoxyribose present in native RNA or DNA. After treatment such as washing to remove excess, unbound antibody-enzyme conjugate from the system it is treated with the enzyme's substrate to produce a detectable signal such as a colored product, indicating the presence of the target nucleic acid in the sample. Labels other than enzymes can, of course, be detected appropriately.

Alternatively, one can envision other binding reagents, such as a lectin, which could be conjugated to an enzyme or other labels. The assay protocol for such a conjugate would be similar to that above.

Arabinonucleic acid probes have several unique advantages. Since one arabinose binding site can be incorporated into each nucleotide of the hybridization probe, each nucleotide is capable of having an anti-arabinose antibody-label bound to it to achieve labeling at the levels usually obtainable with radioisotopes. At the same time, the hazards of radioactive materials are avoided. In addition, these fully labeled probes will not undergo the degradation that radiolabeled probes experience due to lysis by the high-energy decay products of the radiolabels. Furthermore, since detectability of the ANA relies upon the inverted chirality about the C2 carbon atom in the sugar backbone of the probe, and since the chemical bonds about the C2 carbon atom are not involved in determining either the intra- or interstrand structure of the probe or the probe-target hybrid, specificity of the probe and the stability of the probe-target hybrid are not expected to be affected significantly. This higher degree of labeling of the ANA probe, achieved without altering the specificity of the probe for its complementary sequence of bases, makes the probes of this invention superior to the chemically derivatized probes of the prior art. Finally, the arabinose in the probe can be specifically detected using an antibody-enzyme conjugate. The advantage of the use of an enzyme label derives from the high degree of signal magnification due to the large turnover of substrate to product. Thus, use of antibody-enzyme conjugates to detect arabinose possesses not only the advantage of the high degree of probe labeling characteristic of radiolabeled probes but also the signal magnification of an enzyme-based nonradiometric assay.

EXAMPLE 1

A. Chemical Synthesis of Protected Arabinonucleotides for Probe Synthesis

Probe synthesis through chemical polymerization of nucleotides requires the availability of at least four protected and activated arabinonucleotides containing the bases guanine, cytosine, adenine, and uracil or thymine. Each of these protected nucleotides can be prepared from the corresponding nucleosides, which are commercially available.

The addition of protective and activating groups to a nucleoside will be illustrated for the preparation of the protected and activated nucleoside arabinouracil (araU). The other arabinonucleosides were protected and activated in an identical manner; in addition, nucleosides containing the bases cytosine and adenine required protection on the base itself in the form of a benzoyl group while guanine required an isobutyryl protecting group.

First, a dimethoxytrityl (DMT) group was introduced at the hydroxyl on the 5'-carbon of arabinose. This was done by adding 7.75 mmoles of dimethoxytrityl chloride (DMTCl) in eight equal portions at 1-hour intervals to 6.5 mmoles of β-D-arabinouracil dissolved in 30 mL pyridine at −5° C. One hour after the final addition, the reaction mixture was poured into ice water to destroy excess dimethoxytrityl chloride and reduced to a gum at approximately 25° C. on a rotary evaporator. The product, 5'-DMT araU, was isolated from the reaction mixture on a column of Merck Kieselgel 60 silica gel eluted with a 95/5 mixture of chloroform/methanol. Yields of 90–95% were obtained.

A tert-butyldimethylsilyl group (TBDMS) was then introduced at the hydroxyl group on the 3'-carbon of arabinose in the arabinonucleoside. 5'-DMT araU, 5.5 mmoles, prepared as above, was dissolved in dimethoxyethane (110 mL) and 44 mmoles of triethylamine was added. Next, 16.5 mmoles of silver nitrate was added and the mixture stirred for 1 hour at room temperature. Then, 16.5 mmoles of tert-butyldimethylsilyl chloride was added and this reaction mixture stirred for 5 hours at room temperature. The reaction mixture was filtered into a 10% solution of sodium bicarbonate and the aqueous mixture was extracted twice with methylene chloride. The organic extract was evaporated to dryness and 5'-DMT,3'-TBDMS araU was isolated in 75% yield from a Merck Kieselgel 60 silica gel column eluted with ethyl acetate.

A benzoyl (Bz) protecting group was introduced at the hydroxyl on the 2'-carbon of arabinose in the nucleoside by dissolving 5.4 mmoles of the previously prepared 5'-DMT,3'-TBDMS araU in 40 mL of pyridine and cooling to −45° C. An excess (6.6 mmoles) of benzoyl chloride in methylene chloride was added dropwise to the stirred reaction mixture which was held at −45° C. for 30 minutes after addition was complete. The reaction mixture was warmed and held at −20° C. for 2 hours. After addition of water to hydrolyze unreacted benzoyl chloride, the mixture was reduced to a gum on a rotary evaporator and 5'-DMT,3'-TBDMS,2'-Bz araU was isolated on a silica gel column eluted with a 50/50 mixture of toluene and ethyl acetate.

The temporary blocking group (TBDMS) on the hydroxyl on the 3'-carbon was removed by treating 0.78 mmole of 5'-DMT,3'-TBDMS,2'-Bz araU with 2.5 mmoles of 1M tetrabutylammonium fluoride (in THF) at 25° C. for 0.5 hour. The 5'-DMT,2'-Bz araU was isolated from a silica gel column eluted with ethyl acetate.

The final step in the preparation of the nucleotide involved the activation of the hydroxyl group on the 3'-carbon with a phosphine. 5'-DMT,2'-Bz araU (77 μmoles) was dissolved in 0.23 mL of methylene chloride containing 48 μL of diisopropylethylamine. Next, 31 μL of N,N-diisopropylmethylphosphonamidic chloride was added via syringe to the stirred reaction mixture at 20° C. After 15 minutes, the reaction mixture was diluted with ethyl acetate and extracted with aqueous sodium bicarbonate (saturated). The organic layer was separated from the aqueous bicarbonate, dried with $Na_2SO_4$ and reduced on a rotary evaporator to yield the desired activated and protected nucleotide.

B. Probe Synthesis

It is envisioned that synthesis of the oligomeric ANA probe will follow the procedures developed for production of DNA probes using similarly protected and activated deoxynucleotides (M. H. Caruthers, et al., in *Genetic Engineering*, J. Setlow, ed. Volume 4, pp. 1–17). According to these procedures, the first step in the synthesis would be the addition of a starter derivatized arabinonucleoside to a silanolderivatized silica support. This will be done by reacting the appropriate 5'DMT,2'-Bz arabinonucleoside with succinic anhydride. The succinylated arabinonucleoside would be converted to the p-nitrophenyl ester by reaction with p-nitrophenol and dicyclohexyl carbodiimide. The activated nucleoside will be reacted with aminopropylderivatized silica gel in a mixture of dimethylformamide, dioxane, and triethylamine. Unreacted silanol groups on the silica will be blocked by reaction with acetic anhydride. These steps would result in the silica gel having the nucleoside attached to it at the 3'-end and, therefore, this nucleoside will be at the 3'-end of the probe to be synthesized.

The next nucleotide can then be added to the nucleoside attached to the silica support. The silicanucleoside product prepared above will be treated with p-toluenesulfonic acid in acetonitrile to remove the acid-labile dimethoxytrityl group from the hydroxyl group on the 5'-carbon atom of the nucleoside attached to the silica support. The nucleoside on the support will be condensed with the appropriate arabinonucleotide phosphoramidite to add the next nucleotide to the 5'-end of the growing probe. This reaction will be carried out in the presence of tetrazole in dry acetonitrile to facilitate the condensation reaction. The unreacted 5'-hydroxyl group of the arabinonucleoside on the support will be blocked by treatment, for 1–2 minutes, with acetic anhydride in dimethylaminopyridine. The phosphite triester linkage formed by the preceding condensation will be oxidized to a phosphate ester by treatment with a mixture of iodine and 2,6-lutidine in aqueous tetrahydrofuran for 1–2 minutes. This step concludes the addition of a nucleotide to the growing probe. Additional nucleotides can be added by repeating the above reaction sequence starting with the removal of the protective group from the 5'-hydroxyl in arabinose on the 5'-end of the probe.

When the synthesis of the probe sequence is complete, the oligomeric probe will be treated with triethylamine and thiophenol in dioxane to convert the phosphate triesters in each nucleotide linkage to phosphate diesters. The probe then will be cleaved from the silica support by treatment with concentrated ammonium hydroxide at 20° C. for 3 hours. This treatment will also remove the benzoyl protecting groups from the 2'-hydroxyl groups in each arabinose moiety in the probe and any protecting groups from the bases. The oligomeric ANA probe will be isolated by reversed phase liquid chromatography and the final dimethoxytrityl group on the 5'-end of the probe will be removed by treatment with 80% acetic acid to yield the purified ANA probe, which is ready for use in the hybridization assay.

C. Hybridization Procedure

It is envisioned that the protocol for use of ANA probes would follow along the lines of the various hybridization assays commonly utilized and no limitations on the substitution of ANA probes for DNA or RNA probes in any system is foreseen. Initially, the target or sample nucleic acid would be prepared by any convenient procedure. The nucleic acid would be denatured to a single-stranded state by any conventional means. For example, DNA can be denatured by heating it in an appropriate buffer at 95° C. for 5 minutes. Alternatively, denaturation can be effected by treating DNA with 0.25 N NaOH for 10 minutes. In this case, following denaturation, it is necessary to add an equivalent amount of acid (e.g. HCl) to neutralize the solution containing the single-stranded DNA. At this point, it may also be necessary to adjust the ionic strength of the sample to optimize the binding of the DNA to a support. It is advisable to cool the denatured DNA on ice to lower the rate of renaturation of the single-stranded DNA.

The target nucleic acid can be immobilized onto the surface of a support. Classically, the support of choice has been a nitrocellulose membrane. If this material is used, an aliquot of target nucleic acid can either be spotted onto the membrane or slowly filtered through the membrane contained in a device such as a dot-blot or slot-blot manifold. Following application of the target nucleic acid to the nitrocellulose, the membrane is dried and heated in a vacuum oven at approximately 80° for 0.5-2.0 hours to assure secure attachment to the nitrocellulose.

The support material is not necessarily limited to nitrocellulose. For example, charged nylon supports such as Gene Screen TM (E. I. du Pont de Nemours and Co., Inc., Wilmington, Del.) or Biotrans TM (ICN Radiochemicals, Irvine, Calif.) can also be used. The protocols developed by the manufacturers of the membranes should be followed when immobilizing nucleic acids. This applies whether the nucleic acid is being affixed to the membrane in a dot-blot manifold or by one of the transfer protocols (e.g., Southern transfer) commonly used after electrophoretic separation of the sample nucleic acids.

In a different protocol, the target nucleic acid can be immobilized by hybridizing it to a strand of "capture" nucleic acid which is immobilized to a support material. This capture nucleic acid is complementary to a short sequence of bases in the target nucleic acid and specifically captures it from a solution that may contain substantial quantities of other nucleic acid which are of no immediate interest.

The nucleic acid of interest, which has been firmly immobilized to a support material, is in a single-stranded or denatured state and is available for hybridization with an ANA probe containing a complementary sequence of bases. The immobilized target nucleic acid and the support can next be treated with a buffer solution containing generic DNA (e.g., sonicated salmon sperm DNA) to eliminate nonspecific binding sites for the specific ANA probe. Typically, this generic DNA is present in the buffer at a concentration of 100 $\mu$g/ml and 100 $\mu$l of this prehybridization buffer is required for each $cm^2$ of support material. This prehybridization buffer can also contain 10% sodium dextran sulfate, 0.1% sodium dodecyl sulfate, 50% formamide, and SSPE, which is a mixture of sodium chloride, sodium phosphate, and EDTA. In addition, the buffer can also contain Denhardt's reagent, which is a mixture of ficoll, polyvinyl pyrollidone, and bovine serum albumin.

The support to which the nucleic acid is immobilized is prehybridized in this buffer mixture at an elevated temperature (e.g., 37°-65° C.) for a period of time ranging from several hours to overnight in an effort to block sites on the immobilized nucleic acid to which the ANA probe can be attached nonspecifically. Following prehybridization, ANA probe is added to the prehybridization buffer to the desired final concentration, typically 10-100 ng/mL. Hybridization is then carried out at the appropriate elevated temperature (e.g., 37°-65° C.) for an appropriate period of time, usually overnight.

Following hybridization, the support is washed with a series of buffers to remove ANA probe which may be nonspecifically attached to the support. Typically, as this sequence of washes progresses, the concentration of the salt in the buffer is reduced and the temperature of the wash is increased. Following this series of washes, the support is then rinsed with the appropriate buffer to remove any reagents from the wash buffers that may have a detrimental effect on the activity of the antibody-enzyme conjugate to be added later.

D. Production of Antibodies

Either polyclonal or monoclonal antibodies can be used to detect arabinose in the ANA probe molecules. Polyclonal antibodies can be produced by any convenient method used to produce antibodies to modified DNA [e.g., S. Cohn and M. W. Lieberman, J. Biol. Chem. Volume 259, 12456-62 (1984)]. Likewise, monoclonal antibodies can be produced by any of a number of procedures [H. G. Gratzner, Science Volume 218, 474-5 (1982)].

It is believed that an arabinonucleotide conjugated to a suitable carrier protein (e.g. BSA) can also serve as the immunogen in antibody production. However, the ANA probe alone (or hybridized to complementary nucleic acid) would be preferred. Alternatively, the probe can be conjugated to a carrier protein to serve as the immunogen. Okabayashi et al. [Cancer Research Volume 37, 619-624 (1977)] reported production of antibodies to 1-$\beta$-D-arabinofuranosylcytosine (ara-C) in plasma. These antibodies did not cross-react with deoxycytidine or cytidine which differ from ara-C only in the 2'-position. This suggests very strongly that antibodies of suitable specificity for arabinose in ANA, which will not crossreact with deoxyribose in DNA or ribose in RNA, can be developed.

E. Preparation of the Antibody-Enzyme Conjugate

Conjugation of the antibody to an enzyme can be carried out by known methods. For example, the use of glutaraldehyde to link amino groups on the enzyme and the antibody is a common approach [H. Wallin, et al., Cancer Letters Volume 22, 163-170 (1984)]. Using this protocol, the enzyme (e.g. peroxidase) is allowed to react for 18 hours at room temperature with glutaraldehyde. After removal of excess glutaraldehyde in a gel filtration column, the activated enzyme is allowed to react with the antibody for 24 hours at 420 C. The antibody-enzyme conjugate is then purified by dialysis, ammonium sulfate precipitation, and gel filtration chromatography. Conjugation procedures using heterobifunctional crosslinking agents such as those described by J. W. Freytag et al., Clin. Chem., Volume 30, 417–420 (1984), or C. C. Leflar et al., Clin. Chem., Volume 30, 1809–1811 (1984) can also be used. It is expected that peroxidase, β-galactosidase, glucose oxidase, alkaline or acid phosphatase or any other useful enzyme could be conjugated to the antibody (or a fragment thereof) and subsequently used to detect arabinose in the ANA probe.

F. Detection of Hybrids

The hybridized sample would be incubated in a blocking buffer which contains reagents to reduce nonspecific adsorption of the antibody-enzyme conjugate to the membrane. Typically, a buffer containing 1% bovine serum albumin is used. Following treatment with the blocking buffer, the membrane would be incubated with an appropriate antibody-enzyme conjugate for a period of time such that the antibody has an opportunity to recognize and bind to each arabinose moiety in the strands of probe hybridized to target nucleic acid. The antibody-enzyme conjugate would consist of an enzyme covalently linked to an antibody or fragment thereof which is specific for arabinose in the probe.

Following binding of the antibody-enzyme conjugate to the probe, the membrane, which now contains conjugate bound to the probe hybridized to the target nucleic acid, is washed again with a series of buffers to remove unbound and nonspecifically bound conjugate from the support. The appropriate enzyme substrate and/or chromogen is incubated with the product on the support and color development is allowed to proceed for a prescribed period of time. The extent of hybridization could be quantified by measuring the rate of color development or the total color developed after a set time period.

I claim:

1. A probe for the detection of a preselected nucleic acid sequence comprising single stranded arabinonucleic acid consisting essentially of arabinonucleotides having 3' and 5' internucleotide linkages with a base linked at the 1' position, said base being selected from the group consisting essentially of adenine, guanine, cytosine, thymine and uracil, said bases having a sequence complementary to said preselected nucleic acid sequence.

2. A method for identifying a preselected nucleic acid sequence in a sample comprising the steps of:
   (a) rendering the nucleic acid in said sample single-stranded;
   (b) immobilizing the single-stranded nucleic acids onto a support;
   (c) contacting said immobilized single-stranded nucleic acids with a single-stranded arabinonucleic acid consisting essentially of arabinonucleotides having 3' and 5' internucleotide linkages with a base linked at the 1' position, said base being selected from the group consisting essentially of adenine, guanine, cytosine, thymine and uracil, said bases having a sequence complementary to said preselected nucleic acid sequence, under conditions that allow a hybridization reaction to occur;
   (d) washing said support to remove arabinonucleic acid not incorporated into the hybrid formed on the support; and
   (e) determining the presence of arabinonucleic acid in the hybrid formed on the support by contacting it with an anti-arabinose antibody-label conjugate and detecting said label.

3. The method of claim 2 wherein the label is an enzyme.

* * * * *